United States Patent [19]

Jazbec

[11] Patent Number: 5,072,121

[45] Date of Patent: Dec. 10, 1991

[54] BODY CONTOUR DETERMINING APPARATUS FOR A ROTATING GAMMA CAMERA

[75] Inventor: Ivan Jazbec, Wilmette, Ill.

[73] Assignee: Siemens Gammasonics Inc., Hoffman Estates, Ill.

[21] Appl. No.: 614,791

[22] Filed: Nov. 15, 1990

[51] Int. Cl.[5] ........................ G01T 1/166; G01B 11/24
[52] U.S. Cl. ........................ 250/363.04; 250/363.02; 250/221; 356/376
[58] Field of Search .................. 356/376; 250/363.04, 250/363.02, 491.1, 221

[56] References Cited

U.S. PATENT DOCUMENTS

| 4,445,035 | 4/1984 | Ueyama | 250/363.04 |
| 4,593,189 | 6/1986 | Stoub | 250/363.04 |

FOREIGN PATENT DOCUMENTS

| 0107183 | 8/1981 | Japan | 250/363.04 |
| 0055212 | 3/1985 | Japan | 356/376 |
| 0280602 | 12/1987 | Japan | 356/376 |
| 0150610 | 6/1988 | Japan | 356/376 |
| 0261103 | 10/1988 | Japan | 356/376 |

Primary Examiner—F. L. Evans
Attorney, Agent, or Firm—Mark H. Jay

[57] ABSTRACT

An arrangement for determining the planar contour of an object including a plurality of light emitters and detectors positioned in a circular planar array. The circular array surrounds the object whose planar contour is being determined. The light emitters are sequentially energized and the resulting signals from the light detectors are utilized for determining the object's planar contour.

9 Claims, 3 Drawing Sheets

BODY CONTOUR DETERMINING APPARATUS FOR A ROTATING GAMMA CAMERA

BACKGROUND OF THE INVENTION

This invention relates to body scanning apparatus and, more particularly, to apparatus for determining the contour of a scanned body in the plane of rotation of the scan head. In its most immediate sense, this invention relates to gamma cameras such are used to form tomographic images of a patient during a nuclear medicine study.

In single photon emission computed tomography (SPECT) systems of the transaxial rotational camera type, a scanning gamma camera head rotates around the region (head, heart) of the patient to be imaged. This rotation is in a plane generally orthogonal to the cranial-caudal axis of the patient and results in the imaging of a cross-sectional slice of the patient's body. Ideally, it is desirable for the camera head to be as close to the body as possible, because this results in increased sensitivity and, consequently, a better image (if the length of the study is held constant) or a shorter study (if the image quality is held constant).

It is known that the orbit of the camera head can be made noncircular with respect to the patient to decrease the average distance between the camera head and the patient. One device for producing such a noncircular orbit is disclosed in U.S. Pat. No. 4,503,331. In this, an effectively elliptical orbit is achieved by combining a circular rotation of the camera head with a linear movement between the head and the patient.

Devices of this type are not entirely satisfactory because they must be adjusted to match the head orbit with the particular patient to be examined. This adjustment is time-consuming and, consequently, the use of such devices reduces patient throughput and consequently increases study costs.

It is alternatively possible, as is shown in U.S. Pat. No. 4,593,189, to provide a camera head with a proximity detector and to urge the head towards the patient while rotating it around the patient. When the head gets too close to the patient, the proximity detector is triggered and the head is moved away from the patient. This solution has not been implemented; one reason may be that it would be difficult to change collimators on a camera head which is provided with such a device. It would also be difficult to use this solution in a multi-headed camera because it would be highly expensive to provide each head with a proximity detector.

It is therefore a primary object of this invention to provide an apparatus which automatically determines the contour of the body in the imaging plane (thereby eliminating the need for throughput-reducing manual adjustment) without mounting a proximity detector on the rotating camera head.

Another object of the invention is to provide such an apparatus which can be used to implement noncircular orbits in scintillation cameras of the multi-head type.

Another object is, in general, to improve on methods and apparatus of this general type.

SUMMARY OF THE INVENTION

The foregoing and additional objects are attained in accordance with the principles of this invention by providing apparatus for determining the contour of an object in a plane of interest. The apparatus comprises energy emitting means for emitting energy of a form to which the object is substantially opaque; in a preferred embodiment, the energy emitting means are light emitters. The apparatus also comprises energy detecting means for detecting the energy and generating a signal in response to the impingement thereon of the energy exceeding a predetermined threshold; in a preferred embodiment, the energy detecting means may be a photodetector such as a photocell. The apparatus also comprises means operatively coupled to the energy emitting means and the energy detecting means for determining the contour of the object. The energy emitting means is controlled to emit the energy sequentially from each of a first plurality of positions in the plane and surrounding the object. From the energy detecting means is generated a plurality of signals at each of a second plurality of positions in the plane and surrounding the object in response to each energy emission from the energy emitting means. Each of the plurality of received signals corresponds to a unique combination of one of the first plurality of positions and one of the second plurality of positions, and the plurality of received signals are utilized for determining the contour of the object in the plane.

Thus, in accordance with the invention, the contour of the object in the plane is approximated by directing radiation towards the object and identifying where the radiation is interrupted by the object. In a preferred embodiment, this is done in a number of views; in each view a fan beam of light is projected toward the patient and the shadow cast by the patient is registered. Once the views encompass a full rotation about the patient, the patient's contour can be approximated and used to drive the camera head; the spacing of the views and the precision with which the shadow dimensions are known determine the accuracy of the approximation.

BRIEF DESCRIPTION OF THE DRAWINGS

The foregoing will be more readily apparent upon reading the following description in conjunction with the drawings in which like elements in different figures thereof have the same reference numeral and wherein.

DETAILED DESCRIPTION OF A PREFERRED EMBODIMENT

Figure 1:
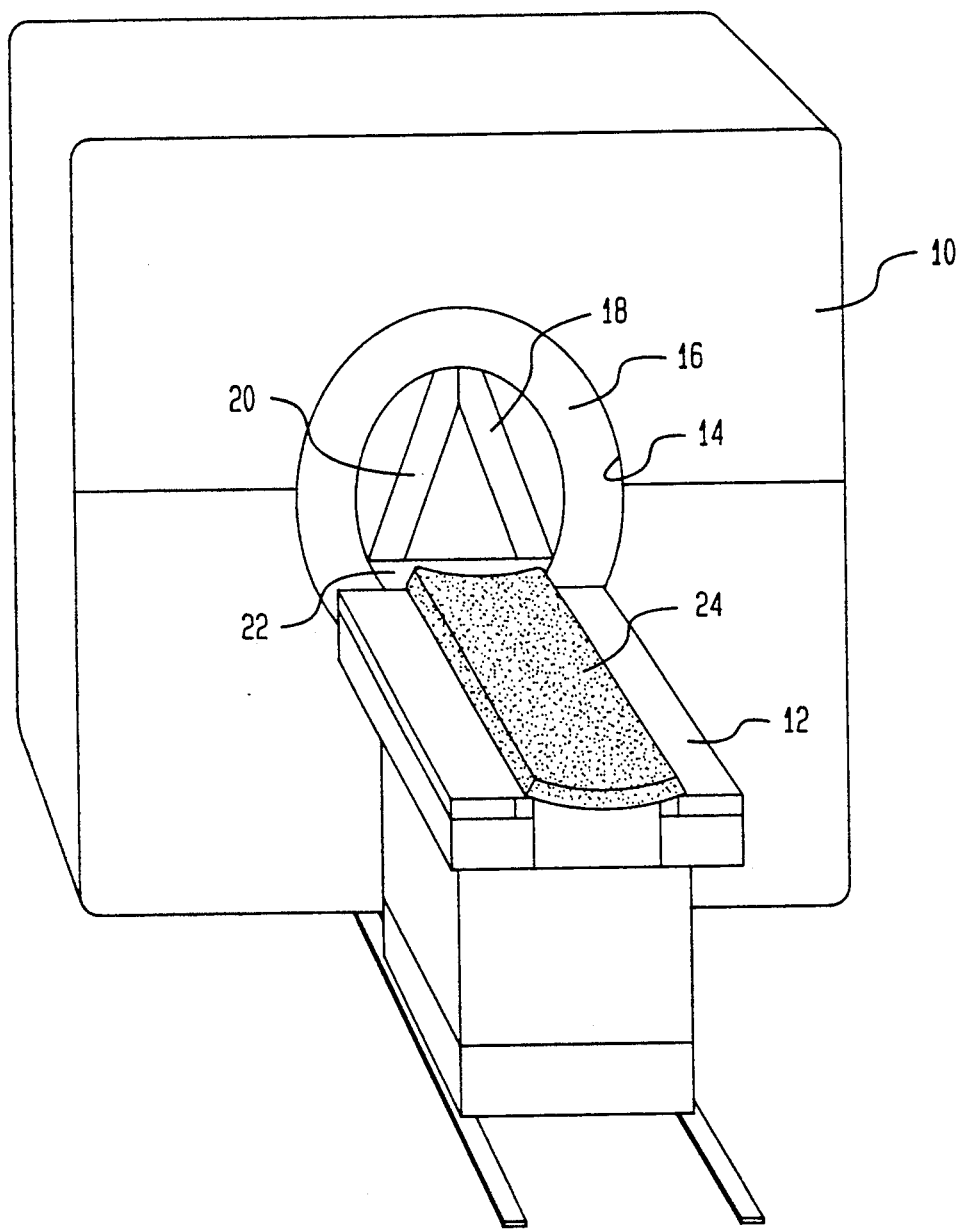
FIG. 1 is a perspective view of a scintillation camera in which the present invention finds utility.

FIG. 1 illustrates a multi-head scintillation camera which is designed to carry out SPECT studies. The camera has a housing 10 with a patient support 12 adjacent thereto. The housing 10 has an opening 14 through which may be seen the gantry which supports and moves the detector heads 18, 20 and 22. The gantry includes a first plate 16 which provides partial support for the detector heads 18, 20 and 22. The patient support 12 includes a slidable pallet 24 which is arranged for movement into and out of the housing 10. This permits a SPECT study to be performed on a patient (not shown in FIG. 1) supported by the pallet 24. Although three heads are illustrated herein, this invention may be practiced in a system having any number of heads. In any event, the heads 18, 20 and 22 are arranged for radial movement with respect to the cranial-caudal axis of the patient as well as for rotation about that axis.

In a SPECT study, the heads 18, 20 and 22 are rotated around the patient so as to collect data for a full 360 degrees around the patient. Advantageously, the heads 18, 20 and 22 should be as close as possible to the patient and should therefore move towards and away from the axis of the patient as the heads rotate about this axis. The present invention contemplates determining the contour of the patient's body in the plane in which the detector heads are to rotate so that the detector heads can follow the patient's body contour as closely as possible during such rotation. Apparatus constructed in accordance with this invention is illustratively located within the housing 10 just inside the opening 14.

Figure 2A:
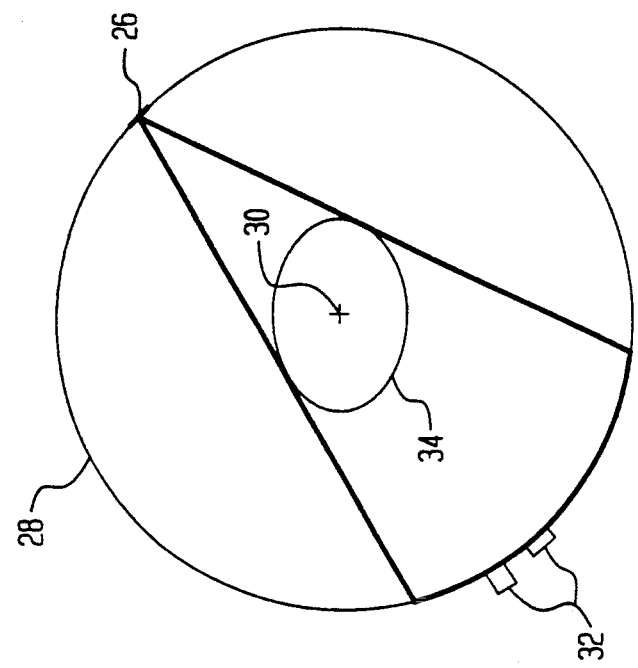
FIGS. 2A and 2B are diagrams useful for illustrating the principles of this invention.
Figure 2B:
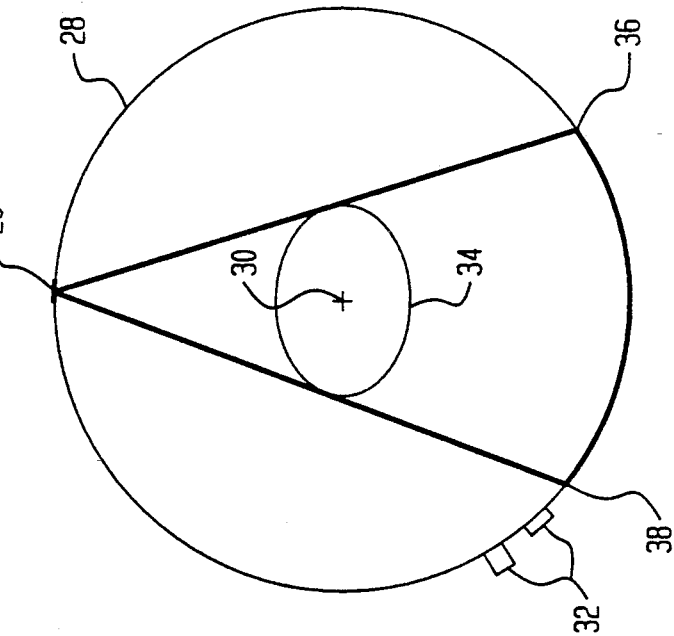

FIGS. 2A and 2B illustrate the principles of this invention. According to this invention, an array of energy emitting devices 26 is positioned along a circle 28 centered at the axis 30 of rotation of the heads 18, 20 and 22. With the patient properly positioned on the pallet 24, the axis 30 corresponds to the patient's cranial-caudal axis. A plurality of energy detecting devices 32 are also positioned along the circle 28. For ease in explanation, the energy emitting devices 26 will be described as light emitters and the energy detecting devices 32 will be described as light detectors. However, it is understood that other forms of energy (e.g. infrared energy) can also be utilized. In any event, the type of energy to be utilized should be chosen so that the body is substantially opaque thereto.

The circle 28 on which are positioned the emitting devices 26 and the detecting devices 32 is preferably in a plane perpendicular to the axis 30. The reference numeral 34 illustrates the contour of the body in the plane of the circle 28. Preferably, there are a plurality of emitting devices 26 positioned along the circle 28 with equiangular spacing therebetween. Similarly, there are a plurality of detecting devices 32 positioned along the circle 28, likewise equiangularly spaced. The number of emitting devices 26 and detecting devices 32 provided is a function of the desired resolution of the system. While a single circle 28 has been shown, it may be desirable in certain applications to have a first circle for the energy emitting devices and a second circle for the energy detecting devices.

When energized, a light emitting device 26 emits light in a fan, rather than in a narrowly focused beam. Each of the light detectors 32 has a broad field of view. When light impinges on a light detector 32, a signal is generated. Lack of light, or an amount of light below a predetermined threshold, results in no signal being generated. (It will be obvious to one skilled in the art that the presence of light need not generate a signal, with a no-signal condition being associated with lack of light. It is alternatively possible that presence of light serves to extinguish a signal which exists when no light is present.) As shown in FIG. 2A, when the illustrated light detector 26 is energized with the body 34 in position, the region on the circle 28 from the point 36 going clockwise to the point 38 will be in shadow and will not be illuminated. Therefore, all light detectors 32 within this shadowed region will not generate a signal. However, the illustrated detectors 32 which are outside the shadowed region will have light impinging thereon and will therefore each generate a signal. As shown in FIG. 2B, if a different light emitter 26 at a different angular orientation on the circle 28 is energized, a different set of light detectors 32 will generate a signal and a different set of light detectors 32 will not generate a signal, as compared with the situation shown in FIG. 2A.

Figure 3:
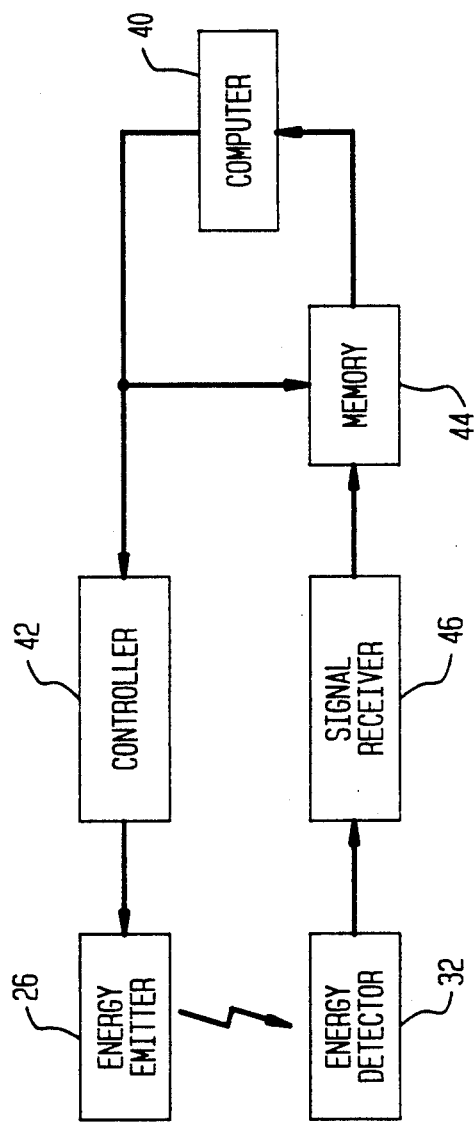
FIG. 3 is a block diagram of a system constructed in accordance with the principles of this invention.

Referring now to FIG. 3, shown therein is a block diagram of an illustrative system for controlling the emitting devices 26 and responding to the signals generated by the detecting devices 32. In FIG. 3, while a computer 40, a controller 42, and a memory 44 are shown as separate elements, these elements may all be part of a single unit. In any event, the controller 42 causes the emitting devices 26 to be energized sequentially around the circle 28. The signals generated by the detecting devices 32 are received by the signal receiver 46 which converts them into a form suitable for storing in the memory 44. The memory 44 is arranged so that the signals are each associated with the particular one of the emitting devices 26 whose energization caused that signal to be generated as well as associated with the particular one of the detecting devices 32 that generated that signal. The computer 40 utilizes the contents of the memory 44 with an internal algorithm to compute the contour 34. This contour 34 is then utilized to control the radial motion of the heads 18, 20 and 22 as they rotate about the axis 30 so that they follow an orbit that is closely spaced to the contour 34.

If a three dimensional object is moved along the axis 30, a number of contours of different planar cross-sections can be derived by repeating the above-described process at each desired cross-sectional location.

A preferred embodiment of this invention has been illustrated with a plurality of emitting devices 26 and detecting devices 32 spaced around a circle 28. Although a circular positioning of the devices 26, 32 is preferred, this is not essential to practicing this invention. Furthermore, a single emitting device 26 and a single detecting device 32 can be utilized by rotating them to different positions about the axis 30. Thus, an emitting device 26 would be energized and the detecting device 32 would be stepped around the axis 30, collecting energy at the different positions. Then the emitting device 26 would be stepped to a new position. The process would then be repeated until the emitting device 26 is back at its starting position.

Accordingly, there has been described an improved arrangement for determining the planar contour of an object. While a single embodiment has been disclosed, it will be apparent to those of ordinary skill in the art that various modifications and adaptations to the disclosed arrangement are possible, and it is only intended that this invention be limited to the scope of the appended claims.

I claim:

1. Apparatus for determining the contour of an object within a plane comprising:
   a plurality of energy emitting devices supported within said plane surrounding said object;
   a plurality of energy responsive devices supported within said plane surrounding said object, each of said energy responsive devices generating a signal in response to the impingement thereon of energy exceeding a predetermined threshold;
   energizing means for sequentially causing said energy emitting devices to emit energy;
   receiving means coupled to said energy responsive devices for receiving the plurality of signals generated by said energy responsive devices in response to the sequential energizations of said energy emitting devices, said receiving means including memory means for storing said received signals and said memory means being organized to store each of said received signals in association with the particular one of said plurality of energy emitting devices whose energization caused the generation of said received signals as well as in association with the particular one of said plurality of energy responsive devices that generated said each of said received signals; and means utilizing the received signals for defining the contour of said object in said plane.

2. The apparatus of claim 1 wherein the energy emitted by said energy emitting devices is light energy.

3. The apparatus of claim 1 wherein said plurality of energy emitting devices are supported in a circular array.

4. The apparatus of claim 3 wherein there are N energy emitting devices which are equiangularly spaced by 360°/N around said circular array.

5. The apparatus of claim 4 wherein said energizing means energizes said energy emitting devices in order around said circular array.

6. Orbit determination apparatus for a body scanner, said body scanner including a scan head adapted for orbital movement around a body in a plane intersecting said body, said apparatus comprising:

an array of selectively energizable energy emitting devices in said plane surrounding said body;

an array of energy detecting devices surrounding said body in said plane, each of said energy detecting devices generating a signal in response to the impingement thereon of energy exceeding a predetermined threshold;

control means for sequentially energizing said energy emitting devices one at a time;

means for receiving the signals generated by said array of energy detecting devices;

means for storing the received signals each in association with a unique combination of an energy emitting device and an energy detecting device;

means utilizing the stored signals for determining the contour of said body in said plane; and means responsive to the determined contour for controlling the movement of the scan head to be in an orbit closely spaced to the contour of said body.

7. The apparatus of claim 6, wherein the body scanner is a scintillation camera.

8. The apparatus of claim 7, wherein the scintillation camera has a plurality of scan heads which rotate in a common plane and which are independently controlled to be in a common orbit closely spaced to the contour of said body.

9. The apparatus of claim 8, wherein the scintillation camera has three scan heads.

* * * * *